United States Patent [19]
Bolanos et al.

[11] Patent Number: 5,911,353
[45] Date of Patent: Jun. 15, 1999

[54] DISPOSABLE LOADING UNIT FOR SURGICAL STAPLER

[75] Inventors: Henry Bolanos, East Norwalk; Alli Alim, Norwalk, both of Conn.; Richard C. McClure, Claremont, Calif.; Keith L. Milliman, Bethel, Conn.

[73] Assignee: United States Surgical Corporation, Norwalk, Conn.

[21] Appl. No.: 09/044,041

[22] Filed: Mar. 18, 1998

Related U.S. Application Data

[63] Continuation of application No. 08/501,197, Jul. 11, 1995, Pat. No. 5,752,644.

[51] Int. Cl.⁶ .................................................. A61B 17/068
[52] U.S. Cl. .......................................... 227/180.1; 227/19
[58] Field of Search ............................. 227/180.1, 175.1, 227/19, 176.1

[56] References Cited

U.S. PATENT DOCUMENTS

| | | |
|---|---|---|
| Re. 34,519 | 1/1994 | Fox . |
| 944,830 | 12/1909 | Sussman . |
| 2,476,249 | 7/1949 | Payne . |
| 2,737,822 | 3/1956 | Morse . |
| 2,885,686 | 5/1959 | Giaimo . |
| 2,975,785 | 3/1961 | Sheldon . |
| 3,060,972 | 10/1962 | Sheldon . |
| 3,071,161 | 1/1963 | Ulrich . |
| 3,079,606 | 3/1963 | Bobrov et al. . |
| 3,090,378 | 5/1963 | Sheldon . |
| 3,162,214 | 12/1964 | Basinet . |
| 3,190,286 | 6/1965 | Stokes . |
| 3,256,875 | 6/1966 | Tsepelve et al. . |
| 3,270,641 | 9/1966 | Gosselin . |
| 3,335,620 | 8/1967 | Vertut . |
| 3,490,675 | 1/1970 | Green et al. . |
| 3,499,591 | 3/1970 | Green . |
| 3,557,780 | 1/1971 | Sato . |
| 3,572,325 | 3/1971 | Bazell et al. . |
| 3,583,393 | 6/1971 | Tahakashi . |
| 3,587,872 | 6/1971 | Pauly . |
| 3,788,303 | 1/1974 | Hall . |
| 3,799,151 | 3/1974 | Fukaumi et al. . |
| 3,892,228 | 7/1975 | Mitsui . |
| 3,998,216 | 12/1976 | Hosono . |
| 4,054,128 | 10/1977 | Seufert et al. . |
| 4,078,555 | 3/1978 | Takahaski . |
| 4,108,211 | 8/1978 | Tanaka . |
| 4,203,430 | 5/1980 | Takahashi . |
| 4,259,876 | 4/1981 | Belyanin et al. . |

(List continued on next page.)

*Primary Examiner*—Scott A. Smith

[57] ABSTRACT

A disposable loading unit is disclosed for use in conjunction with a surgical stapling apparatus configured to sequentially apply a plurality of surgical fasteners to body tissue. The apparatus includes an actuation assembly for effectuating a fastener applying operation, and a housing for receiving and releasably supporting the disposable loading unit. The disposable loading unit includes a staple cartridge body having a longitudinal pathway extending therethrough and a plurality of spaced apart retention slots defined therein each supporting a respective surgical fastener, a plurality of fastener ejection members disposed adjacent the plurality of spaced apart retention slots and communicating with the longitudinal pathway, and an actuator supported within the staple cartridge body and configured to engage the actuation assembly of the apparatus and translate through the longitudinal pathway to contact the fastener ejection members and thereby sequentially eject the surgical fasteners from their respective retention slots.

4 Claims, 16 Drawing Sheets

U.S. PATENT DOCUMENTS

| | | |
|---|---|---|
| 4,273,111 | 6/1981 | Tsukaya . |
| 4,283,165 | 8/1981 | Vertut . |
| 4,290,421 | 9/1981 | Siegmund . |
| 4,347,837 | 9/1982 | Hosono . |
| 4,351,323 | 9/1982 | Ouchi et al. . |
| 4,429,695 | 2/1984 | Green . |
| 4,432,349 | 2/1984 | Oshiro . |
| 4,473,077 | 9/1984 | Noiles et al. . |
| 4,483,326 | 11/1984 | Yamaka et al. . |
| 4,494,417 | 1/1985 | Larson et al. . |
| 4,503,842 | 3/1985 | Takayama . |
| 4,557,254 | 12/1985 | Yamaguchi . |
| 4,593,679 | 6/1986 | Collins . |
| 4,606,343 | 8/1986 | Conta et al. . |
| 4,608,981 | 9/1986 | Rothfuss et al. . |
| 4,688,555 | 8/1987 | Wardle . |
| 4,700,693 | 10/1987 | Lia et al. . |
| 4,718,407 | 1/1988 | Chikama . |
| 4,721,099 | 1/1988 | Chikama . |
| 4,726,355 | 2/1988 | Okada . |
| 4,753,223 | 6/1988 | Bremer . |
| 4,754,909 | 7/1988 | Barker et al. . |
| 4,762,118 | 8/1988 | Lia et al. . |
| 4,762,119 | 8/1988 | Allred, III et al. . |
| 4,770,185 | 9/1988 | Silverstein et al. . |
| 4,773,395 | 9/1988 | Suzuki et al. . |
| 4,779,612 | 10/1988 | Kishi . |
| 4,787,369 | 11/1988 | Allred, III et al. . |
| 4,790,294 | 12/1988 | Allred, III et al. . |
| 4,794,912 | 1/1989 | Lia . |
| 4,796,607 | 1/1989 | Allred, III et al. . |
| 4,805,596 | 2/1989 | Hatori . |
| 4,815,911 | 3/1989 | Bengtson et al. . |
| 4,834,069 | 5/1989 | Umeda . |
| 4,873,965 | 10/1989 | Danieli . |
| 4,905,666 | 3/1990 | Fukuda . |
| 4,911,148 | 3/1990 | Sosonowski et al. . |
| 4,919,112 | 4/1990 | Siegmund . |
| 4,947,827 | 8/1990 | Opie et al. . |
| 4,955,959 | 9/1990 | Thompkins et al. . |
| 4,977,790 | 12/1990 | Nishi et al. . |
| 4,996,974 | 3/1991 | Ciarlei . |
| 5,002,041 | 3/1991 | Chikama . |
| 5,005,558 | 4/1991 | Aomori . |
| 5,007,406 | 4/1991 | Takahasi et al. . |
| 5,014,515 | 5/1991 | Krauter . |
| 5,014,685 | 5/1991 | Takahashi . |
| 5,025,804 | 6/1991 | Kondo . |
| 5,031,814 | 7/1991 | Tompkins et al. . |
| 5,042,707 | 8/1991 | Taheri . |
| 5,065,929 | 11/1991 | Schulze et al. . |
| 5,108,819 | 4/1992 | Wollschlager et al. . |
| 5,125,395 | 6/1992 | Adair . |
| 5,143,475 | 9/1992 | Chikama . |
| 5,156,315 | 10/1992 | Green et al. . |
| 5,158,086 | 10/1992 | Brown et al. . |
| 5,167,221 | 12/1992 | Chikama . |
| 5,168,864 | 12/1992 | Shockey . |
| 5,174,276 | 12/1992 | Crockard . |
| 5,174,277 | 12/1992 | Matsumaru . |
| 5,176,126 | 1/1993 | Chikama . |
| 5,178,129 | 1/1993 | Chikama . |
| 5,179,935 | 1/1993 | Miyagi . |
| 5,195,968 | 3/1993 | Lundquist et al. . |
| 5,307,976 | 5/1994 | Olson et al. . |
| 5,312,023 | 5/1994 | Green et al. . |
| 5,318,221 | 6/1994 | Green et al. . |
| 5,326,013 | 7/1994 | Green et al. . |
| 5,332,142 | 7/1994 | Robinson et al. . |
| 5,391,180 | 2/1995 | Tovey et al. . |
| 5,394,864 | 3/1995 | Kobayashi et al. . |
| 5,411,519 | 5/1995 | Tovey et al. . |
| 5,417,203 | 5/1995 | Tovey et al. . |
| 5,447,265 | 9/1995 | Vidal et al. . |
| 5,478,003 | 12/1995 | Green et al. . |
| 5,485,947 | 1/1996 | Olson et al. . |
| 5,489,058 | 2/1996 | Plyley et al. . |
| 5,632,432 | 5/1997 | Schulze et al. ............ 227/180.1 |
| B1 5,040,715 | 8/1991 | Green et al. . |

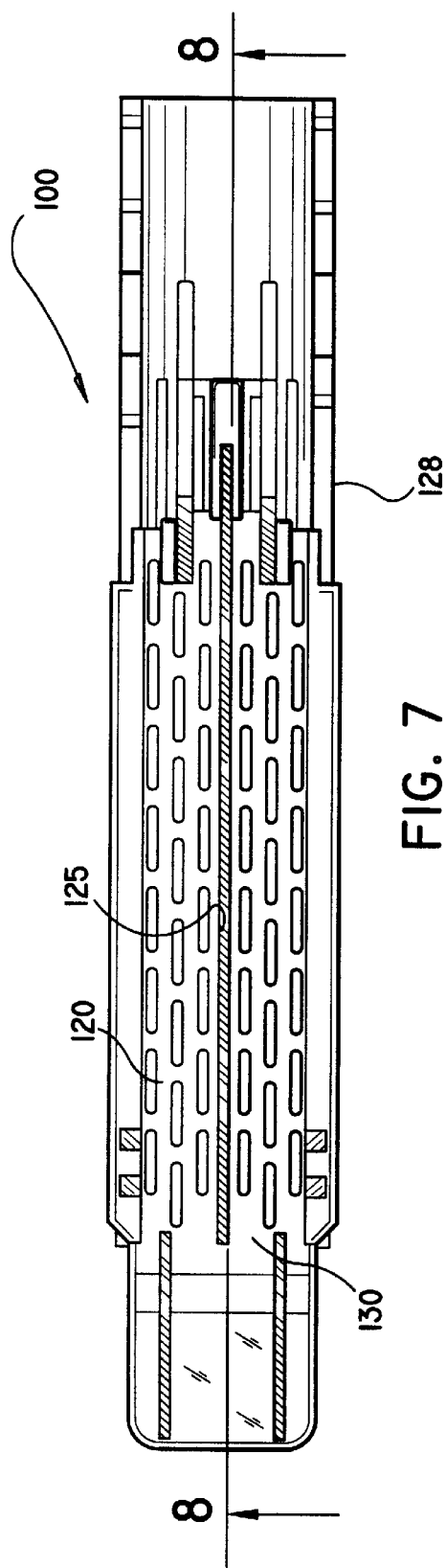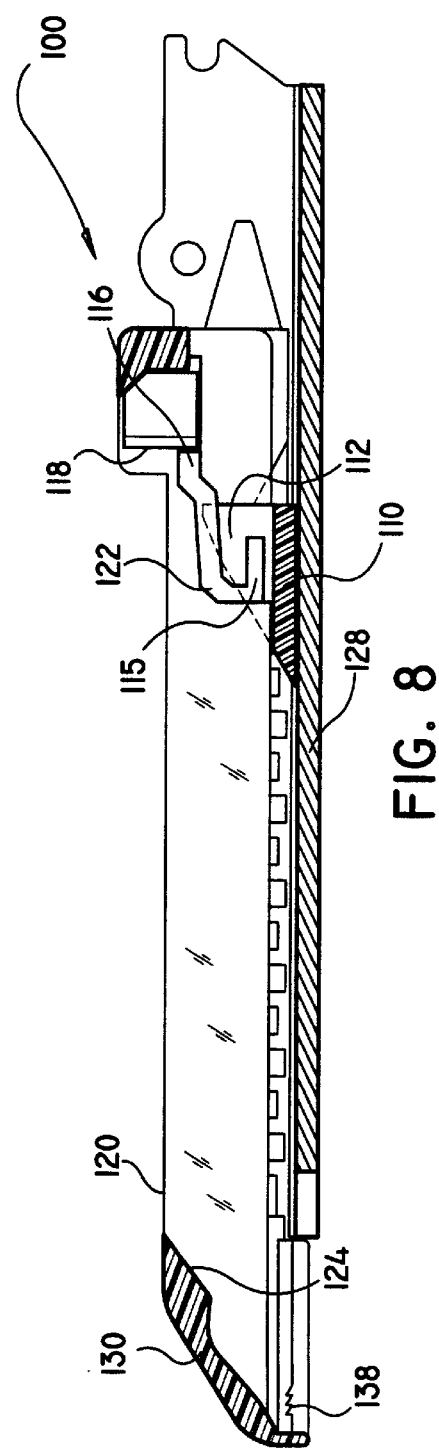

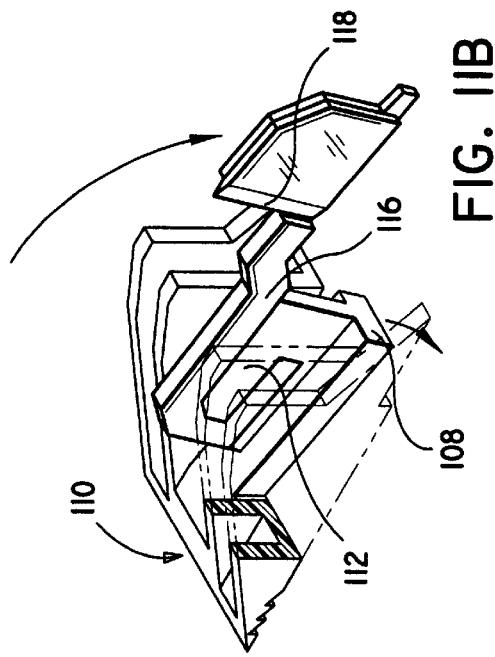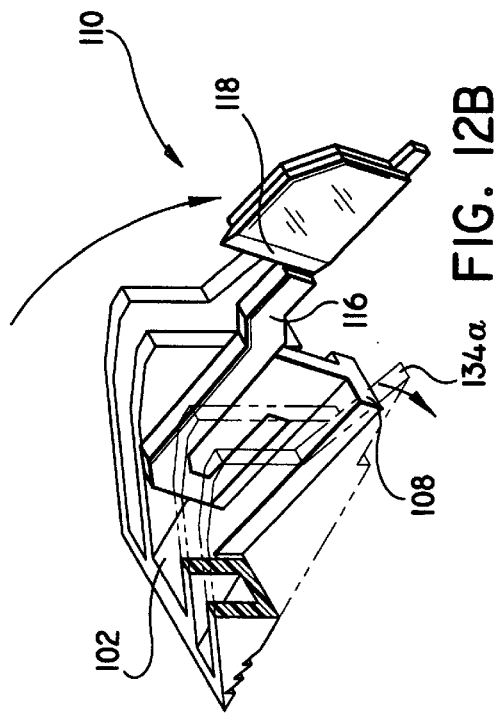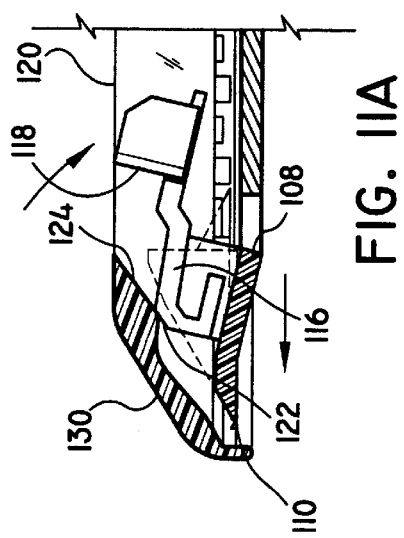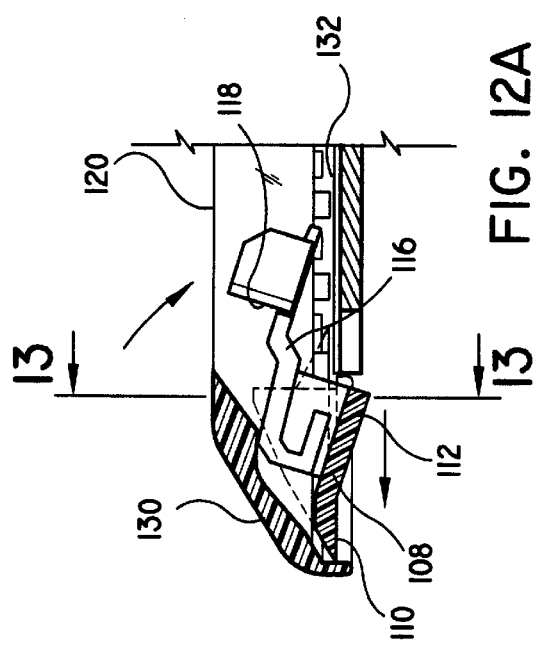

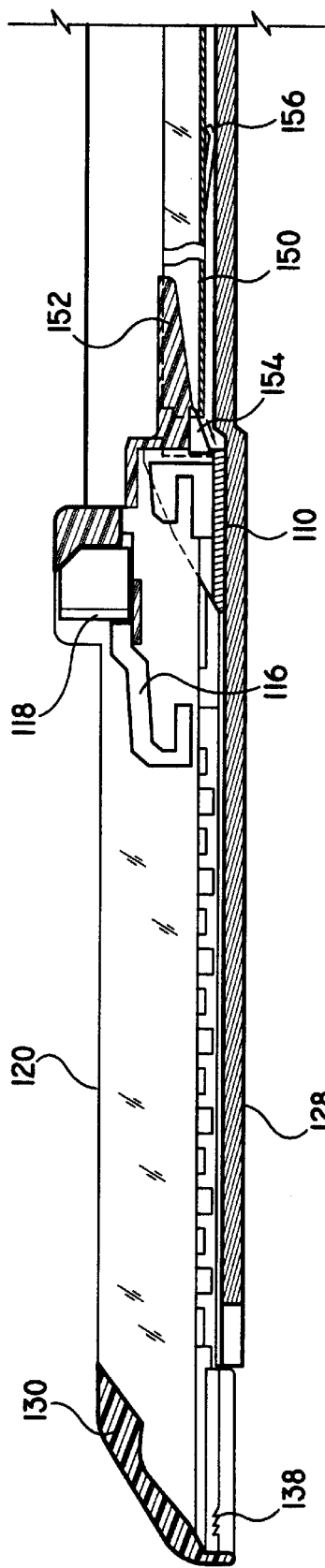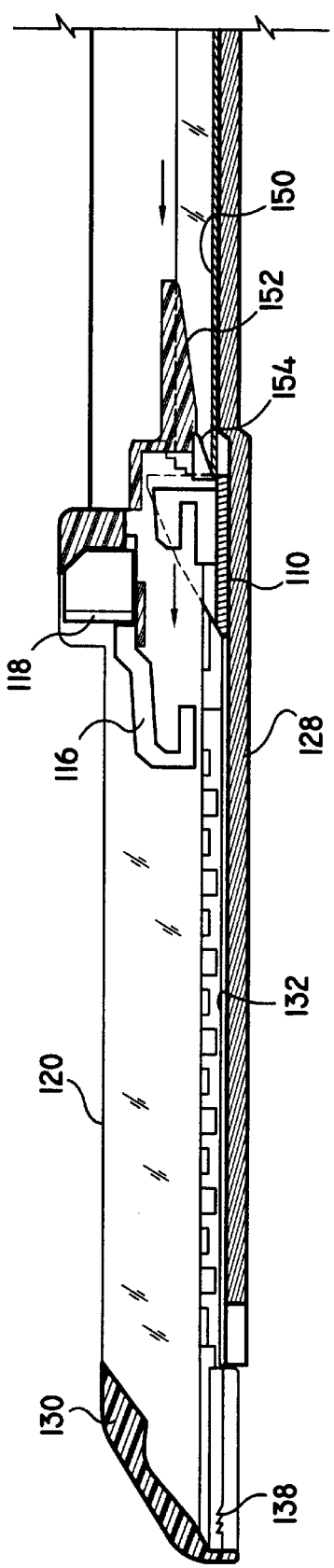

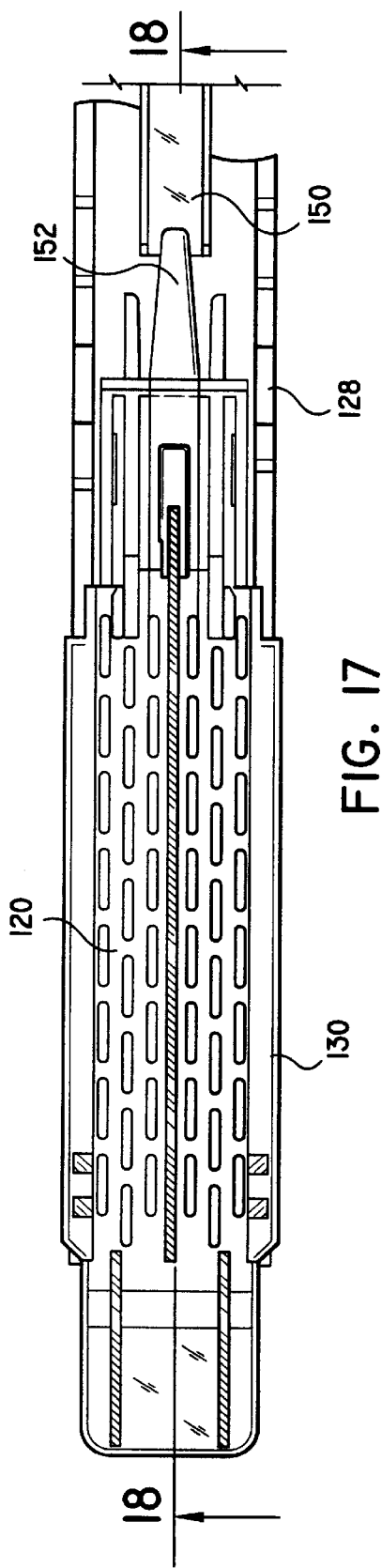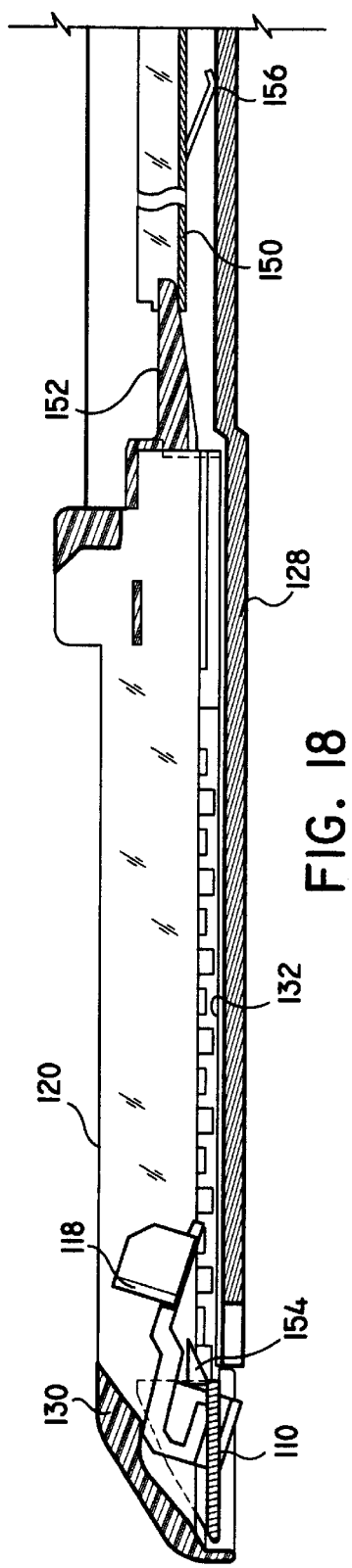
FIG. 17
FIG. 18

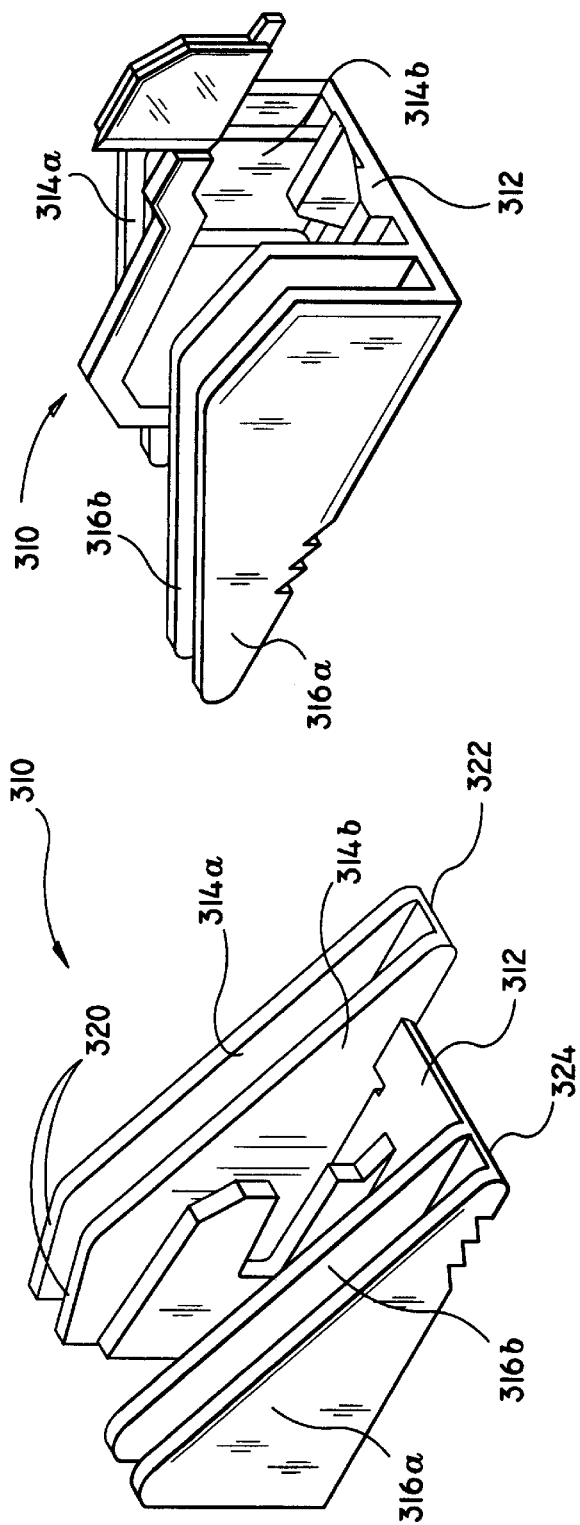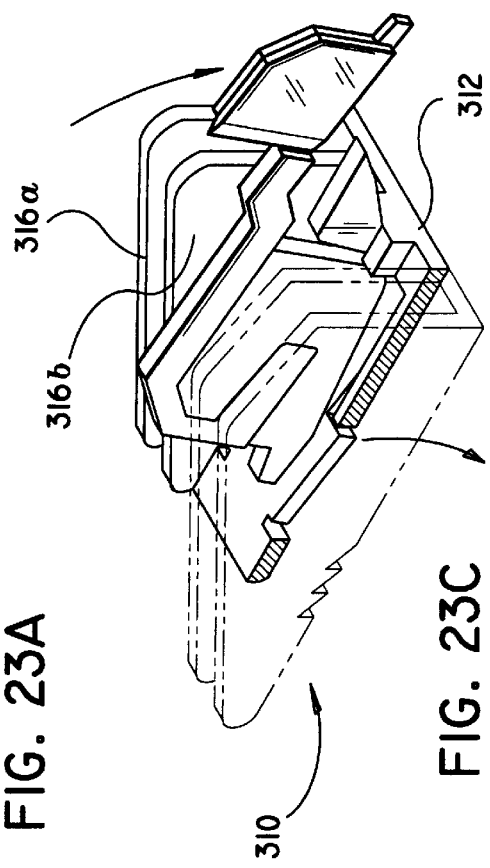
FIG. 23A
FIG. 23B
FIG. 23C

DISPOSABLE LOADING UNIT FOR SURGICAL STAPLER

This application is a continuation of U.S. application Ser. No. 08/501,197 filed Jul. 11, 1995, now U.S. Pat. No. 5,752,644.

BACKGROUND

1. Technical Field

This invention relates to a disposable loading unit for a surgical stapler, and more particularly, to a disposable loading unit for an apparatus configured to sequentially apply a plurality of surgical fasteners to body tissue and optionally incise the fastened tissue.

2. Background of Related Art

Surgical devices wherein tissue is first grasped or clamped between opposing jaw structure and then joined by surgical fasteners are well known in the art. In some instruments a knife is provided to cut the tissue which has been joined by the fasteners. The fasteners are typically in the form of surgical staples but two part polymeric fasteners can also be utilized.

Instruments for this purpose can include two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. No. 3,079,606 and U.S. Pat. No. 3,490,675.

A later stapler disclosed in U.S. Pat. No. 3,499,591 applies a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam to effect ejection of the staples. Other examples of such staplers are disclosed in U.S. Pat. Nos. 4,429,695 and 5,065,929.

Each of the instruments described above were designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. Nos. B5,040,715 (Green, et al.); 5,307,976 (Olson, et al.); 5,312,023 (Green, et al.); 5,318,221 (Green, et al.); 5,326,013 (Green, et al.); and 5,332,142 (Robinson, et al.).

U.S. Surgical, the assignee of the present application, has manufactured and marketed endoscopic stapling instruments, such as the Multifire ENDO GIA* 30 and Multifire ENDO GIA* 60 instruments, for several years. These instruments have provided significant clinical benefits. Nonetheless, improvements are possible, for example, by reducing the cost and complexity of manufacture and/or reducing the amount of material discarded at the conclusion of a surgical procedure. In making any such improvements, it would be highly desirable not to sacrifice any of the important benefits of the MULTIFIRE ENDO GIA* 30 and 60 instruments as compared to other commercially available products, e.g., the endoscopic stapling instruments manufactured and marketed by Ethicon, Inc. For example, any improvement should advantageously provide a fresh knife blade for each firing of the instrument and ensure that the disposable loading unit is securely retained in the stapling instrument unless and until the operating team chooses to remove it. These advantages have historically been found in the U.S. Surgical instruments, but not in the Ethicon instruments.

Therefore, a need exists for a disposable loading unit that exhibits all of the benefits of the present assignee's commercially available instruments while also reducing the cost and complexity of manufacture and/or reducing the amount of material discarded at the conclusion of a surgical procedure.

SUMMARY

The subject application is directed to a disposable loading unit for a surgical stapling apparatus configured to sequentially apply a plurality of surgical fasteners to body tissue during a surgical procedure. The apparatus with which the disposable loading unit is associated includes an actuation assembly for effectuating a fastener applying operation, and a housing mountable to a surgical stapling instrument for receiving and detachably supporting the disposable loading unit. The housing may be removably mounted to the stapler apparatus.

The disposable loading unit includes a staple cartridge body having a longitudinal pathway extending therethrough and a plurality of spaced apart retention slots defined therein each supporting a respective surgical fastener, a plurality of fastener ejection members disposed within the plurality of spaced apart retention slots and communicating with the longitudinal pathway. The disposable loading unit also includes an actuator supported within the staple cartridge body and configured to engage the actuation assembly of the apparatus and translate through the longitudinal pathway to contact the fastener ejection members and thereby sequentially eject the surgical fasteners from their respective retention slots.

The actuator includes a base portion and at least two upstanding parallel cam plates each preferably defining an angled leading edge for contacting the fastener ejection members. In one embodiment, the leading edge of each cam plate is configured to controllably deform as the actuator translates through the staple cartridge body. Alternatively, each of the cam plates is configured to be reduced in size or mass as the actuator translates through the staple cartridge body. In a further alternative embodiment, the cam plates can be fabricated from a rigid material that does not significantly deform during fastener ejection.

The disposable loading unit can also include an optional cutting member that is configured to translate through the staple cartridge body in association with the actuator to form an incision in the stapled body tissue. In operation, the cutting member intersects the tissue contacting plane during its translation through the staple cartridge body, and is moved out of intersection with the tissue contacting plane at the conclusion of a stapling operation. The cutting member is single use only, thereby ensuring maximum sharpness for each firing.

In a preferred embodiment of the disposable loading unit, structure is associated with the disposable loading unit for releasably engaging the housing to inhibit movement of the disposable loading unit within the housing during a fastener applying operation. Structure associated with the disposable loading unit for releasably engaging the housing includes a pair of elongate struts dimensioned and configured to engage the opposed side walls of the housing to inhibit lateral movement of the disposable loading unit. A pair of opposed detents which are dimensioned and configured to engage a pair of corresponding notches defined in the opposed side walls of the housing can also be provided to inhibit longitudinal movement of the disposable loading unit. Furthermore, a pair of opposed outwardly extending protuberances which are dimensioned and configured to engage a pair of corresponding indentations defined in the opposed side walls of the housing can be provided to inhibit vertical movement of the disposable loading unit. The disposable loading unit can also include a pair of spaced apart wings which extend from a proximal end of the staple cartridge body and include angled guide surfaces for guiding the disposable loading unit into the housing during assembly.

In another preferred embodiment of the disposable loading unit, at least one camming surface is provided for facilitating engagement of the actuator and the actuation assembly of the surgical apparatus to enable the performance of a fastener applying operation. Preferably, a first cam wing depends from a proximal end of the staple cartridge body and defines a first angled cam surface, and a second cam wing depends from a proximal end of the actuator and defines a second angled cam surface. When the first and second angled cam surfaces are aligned, the actuation assembly of the stapler can engage the actuator and drive it through the staple cartridge body. However, when the angled cam surfaces are spaced from one another, i.e. when the actuator is at the distal end of the staple cartridge body, the actuation assembly will be unable to engage the actuator and the apparatus will be rendered inoperative until the used disposable loading unit is removed from the apparatus.

In another preferred embodiment, structure is provided on the fastener actuator and the staple cartridge body for retaining the actuator at the distal end of the staple cartridge body after the fasteners have been fired.

Advantageously, the disposable loading unit disclosed herein provides a replaceable unit which preserves the advantage of a disposable loading unit over a replaceable staple cartridge; namely, providing new cam plates and/or knife with each disposable loading unit.

Further features of the surgical apparatus will become more readily apparent to those skilled in the art from the following detailed description of the invention taken in conjunction with the drawings.

BRIEF DESCRIPTION OF THE DRAWINGS

Various preferred embodiments of the disposable loading unit of the subject application will be described hereinbelow with reference to the drawings wherein:

FIG. 7 is a top plan view of the disposable loading unit of FIG. 6;

FIG. 8 is a side elevational view in cross-section taken along line 8—8 of FIG. 7 with the actuator disposed in a proximal position within the staple cartridge body;

FIG. 11A is a side elevational view in cross-section of the distal portion of the disposable loading unit as the cutting blade is moved out of intersection with the tissue contacting surface of the staple cartridge body;

FIG. 11B is a perspective view of the actuator and cutting blade carrier in an orientation corresponding to their respective positions shown in FIG. 11A;

FIG. 12A is a side elevational view in cross-section of the distal portion of the disposable loading unit with the cutting blade moved out of intersection with the tissue contacting surface of the staple cartridge body;

FIG. 12B is a perspective view of the actuator and the cutting blade carrier in an orientation corresponding to their respective positions shown in FIG. 12A;

FIG. 15 is a side elevational view in cross-section of a disposable loading unit and housing constructed in accordance with a preferred embodiment prior to a fastening procedure wherein the actuator is disposed in a proximal position, spaced from the cutting blade carrier, and partially engaged by an actuation channel;

FIG. 16 is a side elevational view in cross-section of the disposable loading unit illustrated in FIG. 15 with the actuator fully engaged by the actuation channel;

FIG. 17 is a top plan view of the disposable loading unit, housing, and actuation channel;

FIG. 18 is a side elevational view in cross-section taken along line 18—18 of FIG. 17 illustrating the actuator and cutting blade in a locked position at the distal end of the staple cartridge body, and the actuation channel disposed in a retracted and elevated position adjacent the proximal end of the disposable loading unit;

FIG. 21A is an enlarged view of the indicated area of detail of FIG. 21;

FIG. 21B is an enlarged view of the indicated area of detail of FIG. 21;

FIGS. 23A–23C are perspective views of another actuator constructed in accordance with a preferred embodiment which has staggered cam plates to balance fastener driving forces during a fastening operation.

DETAILED DESCRIPTION OF PREFERRED EMBODIMENTS

Figure 1:
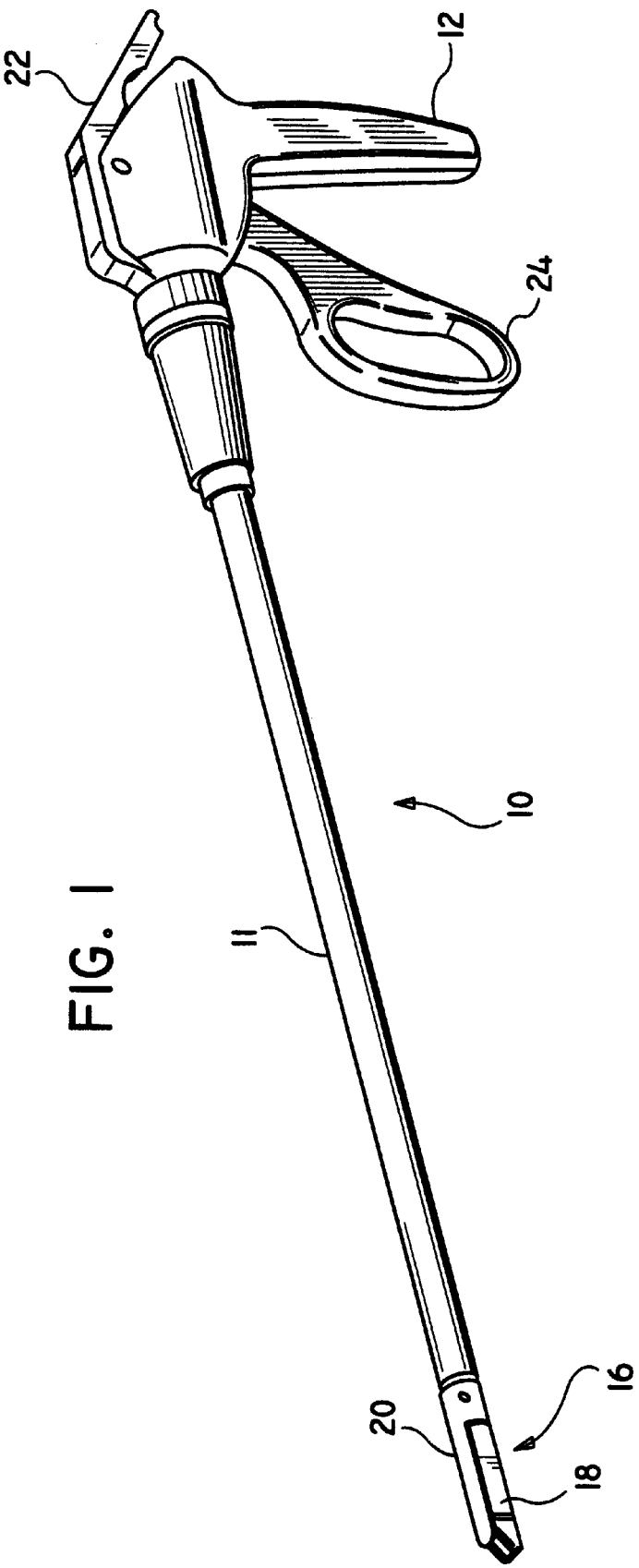
FIG. 1 is a perspective view of a surgical stapling apparatus which employs a disposable loading unit constructed in accordance with a preferred embodiment.
Figure 2:
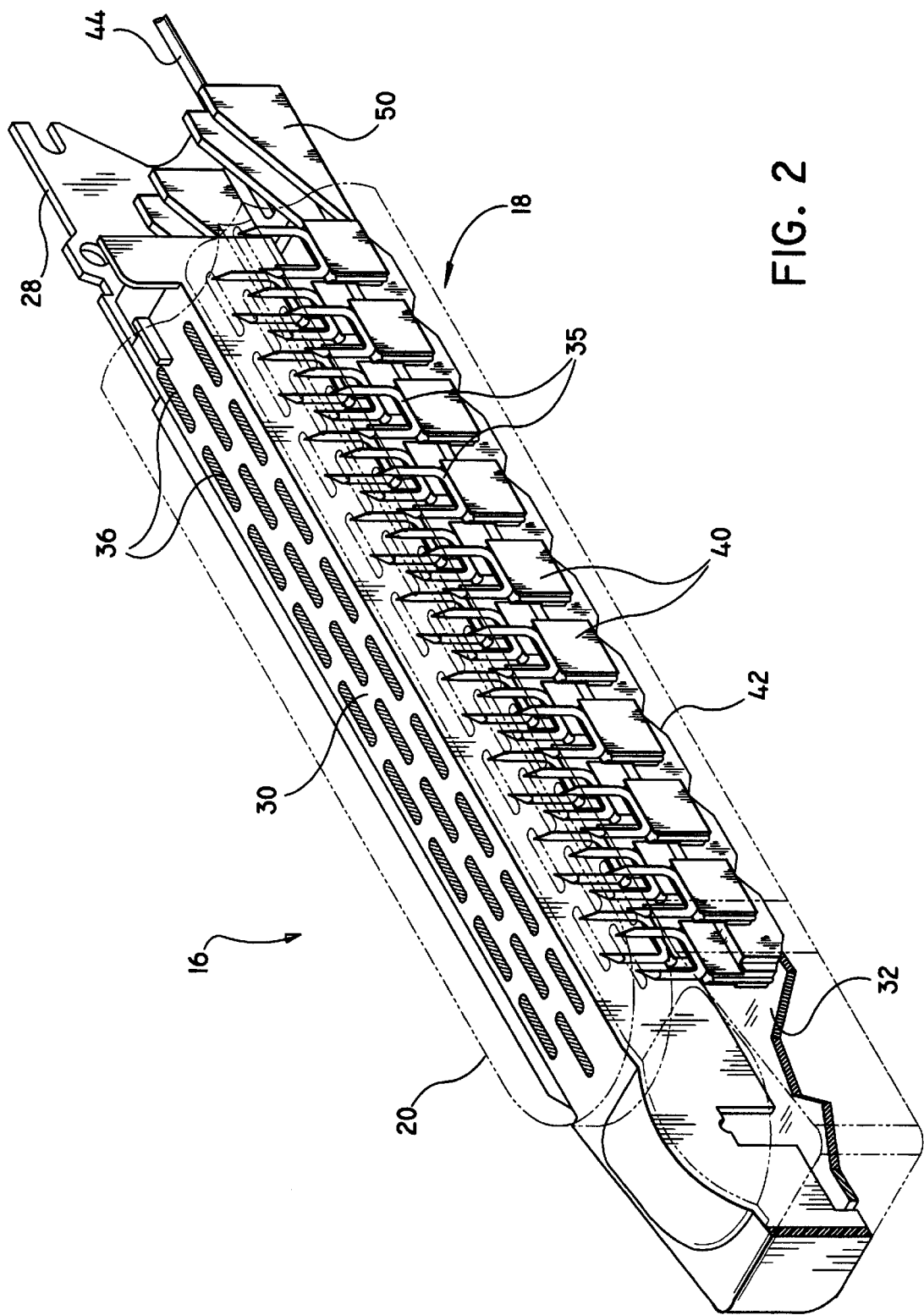
FIG. 2 is a perspective view of a disposable loading unit constructed in accordance with a preferred embodiment and illustrating the position of the actuator prior to a fastener applying operation.

In the drawings and in the description which follows, the term "proximal", as is traditional, will refer to the end of the stapling apparatus which is closest to the operator, while the term "distal" will refer to the end of the apparatus which is furthest from the operator.

The stapling apparatus with which the disposable loading unit of the present disclosure is associated shall be discussed in terms of both conventional and endoscopic procedures. However, use herein of terms such as "endoscopic", "endoscopically", and "endoscopic portion", among others, should not be construed to limit the present apparatus for use only in an endoscopic environment. To the contrary, it is believed that the apparatus and disposable loading unit described herein may find use in procedures wherein access is limited to a small incision including but not limited to arthroscopic and/or laparoscopic procedures, and in other non-endoscopic procedures.

Referring now to the drawings wherein like reference numerals identify similar structural elements of the subject apparatus, there is illustrated in FIG. 1 a surgical stapling apparatus designated generally by reference numeral 10. Stapling apparatus 10 is configured for utilization during laparoscopic and endoscopic surgical procedures and includes a handle assembly 12, an elongated body portion 14, and a fastener applying assembly 16 which is associated with a distal end of elongated portion 14. Fastener applying assembly 16 includes a fastener containing portion 18 and an anvil member 20. Handle assembly 12 includes a clamping handle 22 for effectuating approximation of anvil member 20 and fastener containing portion 18, and an actuation handle 24 for effectuating a fastener applying operation. A stapling apparatus of this type is disclosed in commonly assigned U.S. Pat. No. 5,318,221, the disclosure of which is herein incorporated by reference.

Referring now to FIGS. 2–5A, the fastener containing portion 18 of fastener applying assembly 16 includes a housing 28 dimensioned and configured to receive and detachably support a disposable loading unit. The disposable loading unit includes a staple cartridge body 30 having a longitudinal pathway 32 extending therethrough, and a plurality of spaced apart fastener retention slots 36 formed therein. Each retention slot 36 is dimensioned and configured to support a respective surgical fastener 35 as shown. A plurality of fastener ejectors 40 are also supported within the staple cartridge body 30 and are each associated with surgical fasteners 35. As shown, ejectors 40 are each preferably associated with three surgical fasteners. However, other quantities of surgical fasteners can be associated therewith, such as one or two fasteners per ejector. Each ejector 40 has an angled camming surface 42 which is dimensioned and configured to engage an actuator 50, included in the disposable loading unit, as the actuator translates through pathway 32 under the influence of an actuation shaft or channel 44 of the stapling apparatus. Actuation channel 44 is configured to translate through the body portion 14 of surgical apparatus 10 and is controlled through manipulation of the actuation handle 24 of handle assembly 12.

Figure 3:
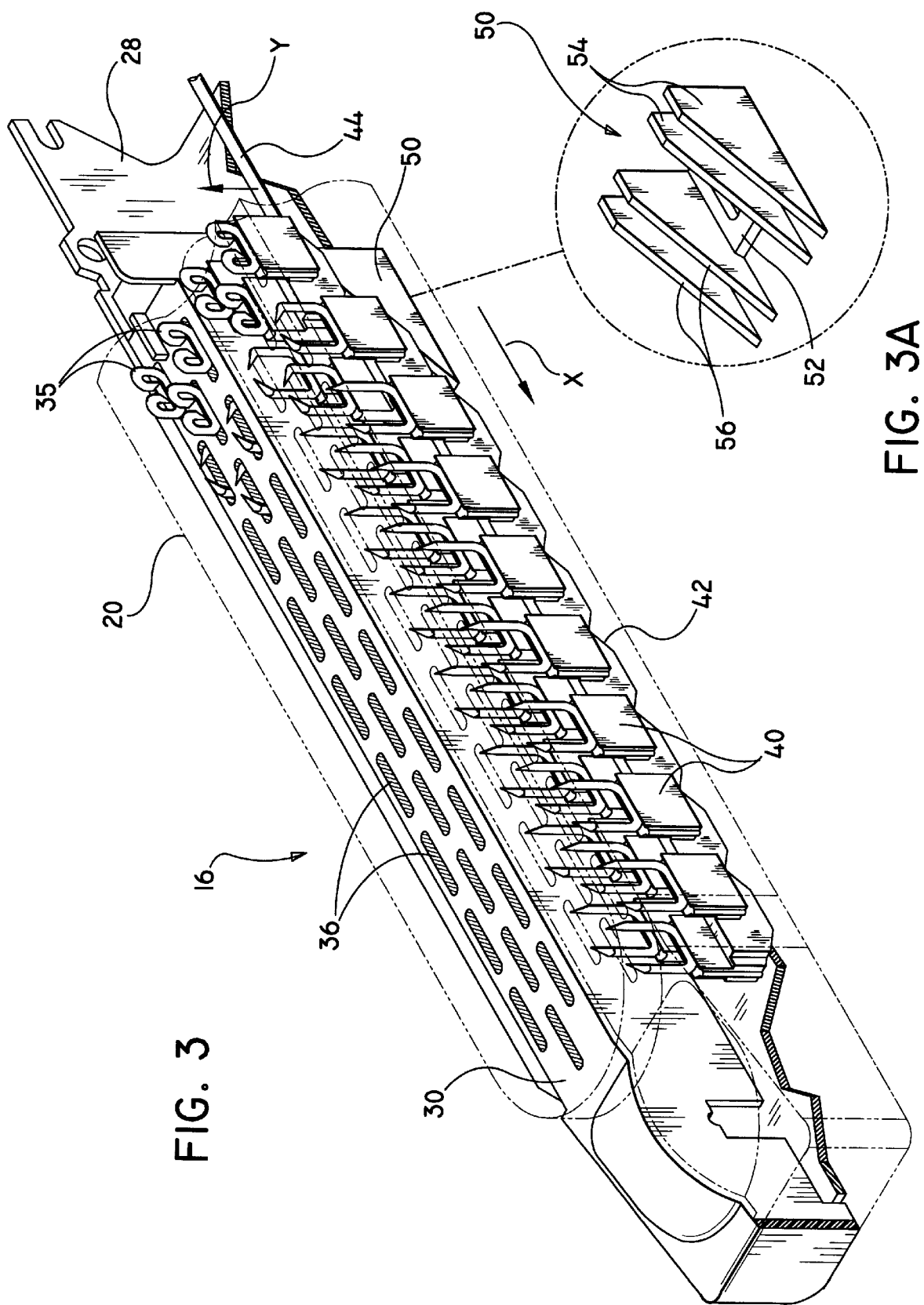
FIGS. 3–5 are perspective views of the disposable loading unit of FIG. 2, during a fastener applying operation as the actuator translates through the staple cartridge body to sequentially eject surgical fasteners from the staple cartridge and drive them against the anvil member to be formed thereby.
Figure 4:
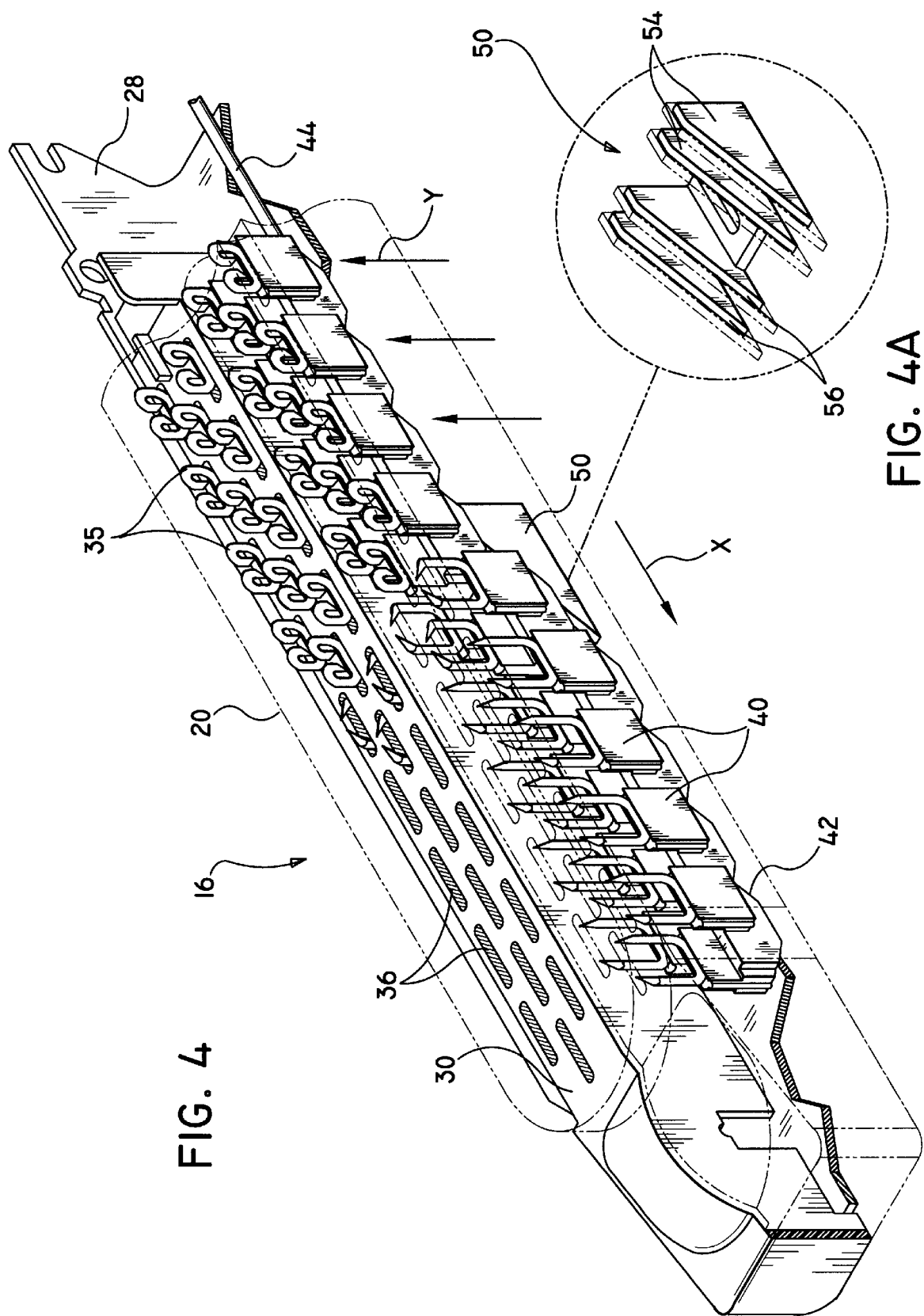
Figure 5:
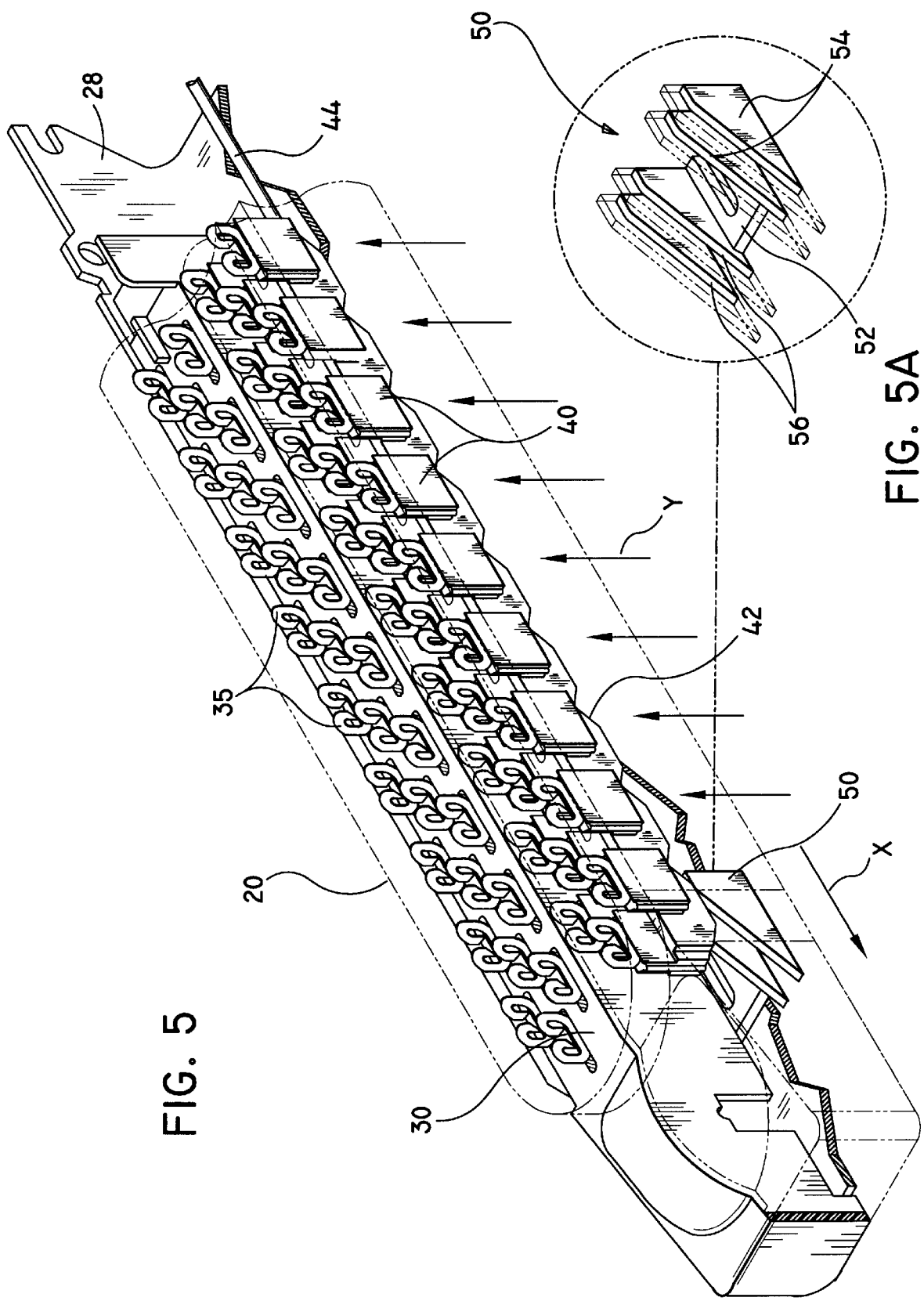

As best seen in FIGS. 3 and 3A, actuator 50 includes a base portion 52 and four spaced apart upstanding cam plates 54. Each cam plate 54 has an angled camming surface 56 for sequentially engaging the camming surface 42 of each fastener ejector 40 as actuator 50 translates through pathway 32. Once contacted or engaged by actuator 50, each ejector 40 is driven vertically in the direction indicated by arrow "Y", urging three adjacent fasteners 35 from their respective retention slots 36 to be driven and formed against the fastener forming surface of anvil member 20 (shown in phantom).

Referring to FIGS. 3–5A, cam plates 54 can be formed of a material such as plastic, or a fibrous composite, which deforms as actuator 50 translates distally and engages fastener ejectors 40. More particularly, cam plates 54 are configured to reduce in mass or decrease in size as actuator 50 is driven through staple cartridge body 30 in the direction indicated by arrow "X". The reduction in mass and the decrease in size results from the forced frictional contact between the camming surfaces 56 of cam plates 54 and the camming surfaces 42 of fastener ejectors 40 under the influence of actuation shaft 44. To compensate for the change in size of actuator 50, ejectors 40 can gradually increase in vertical height to maintain consistent staple formation. Cam plates 54 can also be fabricated from a relatively non-deformable material such as, for example, stainless steel which will not significantly deform.

Following a fastener applying procedure illustrated in FIGS. 3–5A, the disposable loading unit including staple cartridge body 30 together with the actuated fastener ejectors 40 and the displaced actuator 50, is removed from housing 28, discarded, and replaced with a new fully loaded disposable loading unit that includes fasteners, ejectors, and a new actuator.

Figures 6, 6A:
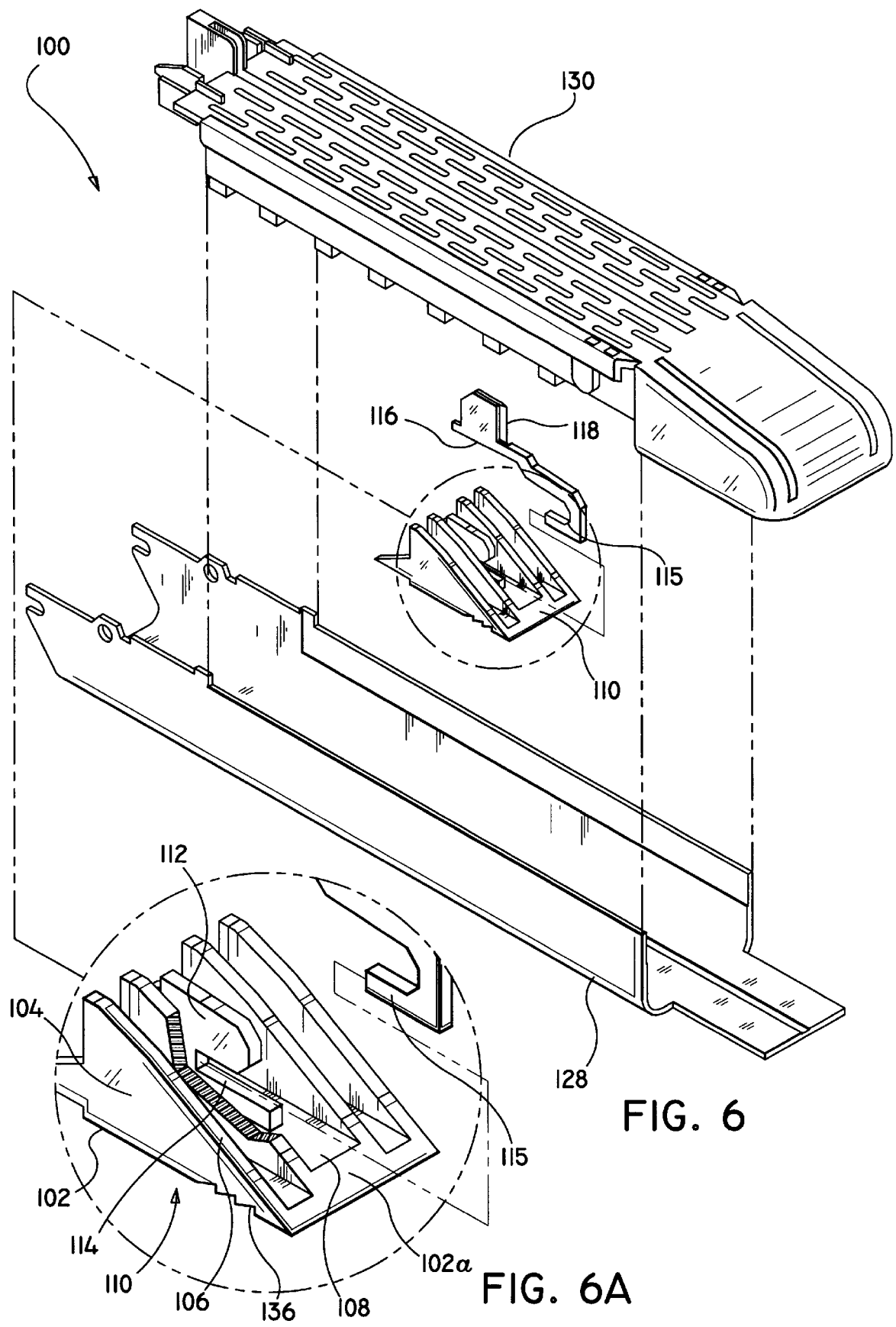
FIG. 6 is an exploded perspective view of another disposable loading unit constructed in accordance with a preferred embodiment that has a cutting blade associated with the actuator.
FIG. 6A is an enlarged view of the indicated area of detail of FIG. 6.

Referring now to FIGS. 6 and 6A, there is illustrated an alternative disposable loading unit 100 constructed in accordance with a preferred embodiment. The disposable loading unit is received in housing 128 and includes an alternative actuator 110. Actuator 110 includes a base portion 102 having an angled leading edge 102a, and four spaced apart upstanding cam plates 104 each defining a respective camming surface 106 in angular alignment with leading edge 102a. Base portion 102 includes a deflectable beam section 108 which supports an upstanding shank 112. A slot 114 is formed in shank 112 for receiving and engaging a correspondingly dimensioned and configured flange 115 associated with blade carrier 116 as actuator 110 begins its translation through staple cartridge body 130. Blade carrier 116 supports knife blade 118 which incises stapled body tissue as actuator 110 translates through staple cartridge body 130 during a fastener applying operation.

As best seen in FIG. 7, a longitudinal slot 125 is formed in staple cartridge body 130 for accommodating the longitudinal translation of knife blade 118 as it intersects the tissue contacting surface 120 of staple cartridge body 130 to engage and form an incision in stapled body tissue. As knife blade 118 approaches the distal end of pathway 132, it is advantageously moved out of the plane defined by tissue contacting surface 120, to prevent injurious contact therewith during removal of the disposable loading unit from housing 128. Alternatively, it is contemplated that the disposable loading unit can further include housing 128, such that the disposable loading unit includes the staple cartridge, actuator and housing.

Figure 9:
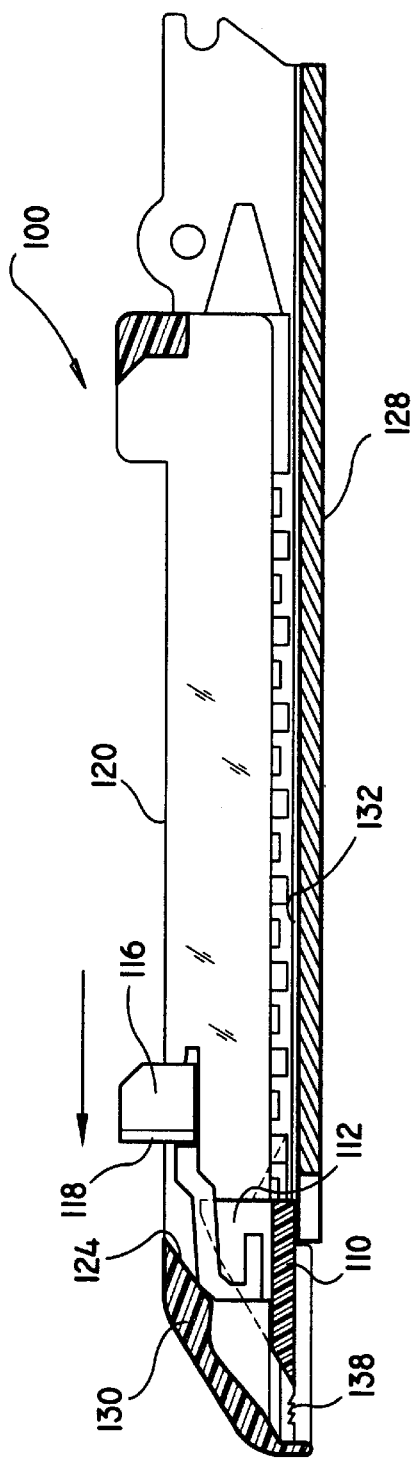
FIG. 9 is a side elevational view of the disposable loading unit of FIG. 8, with the actuator disposed in a distal position prior to the cutting blade being moved out of intersection with the tissue contacting surface of the staple cartridge body.
Figure 10B:
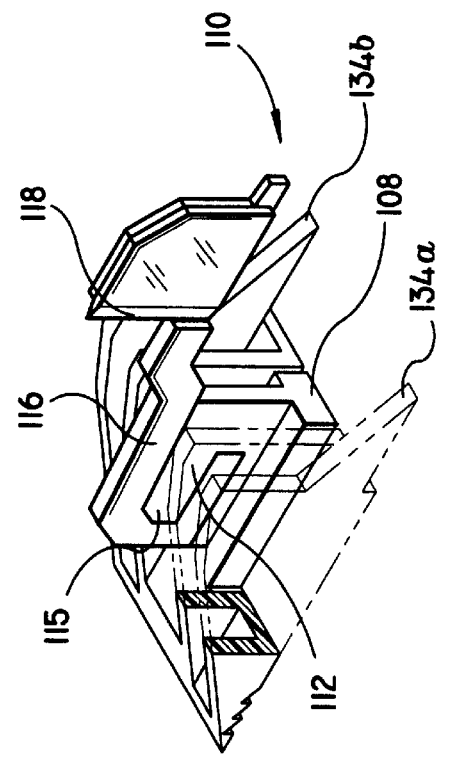
FIGS. 10A and 10B are perspective views of the actuator and the cutting blade carrier in an orientation corresponding to their respective positions shown in FIG. 9.
Figure 10A:
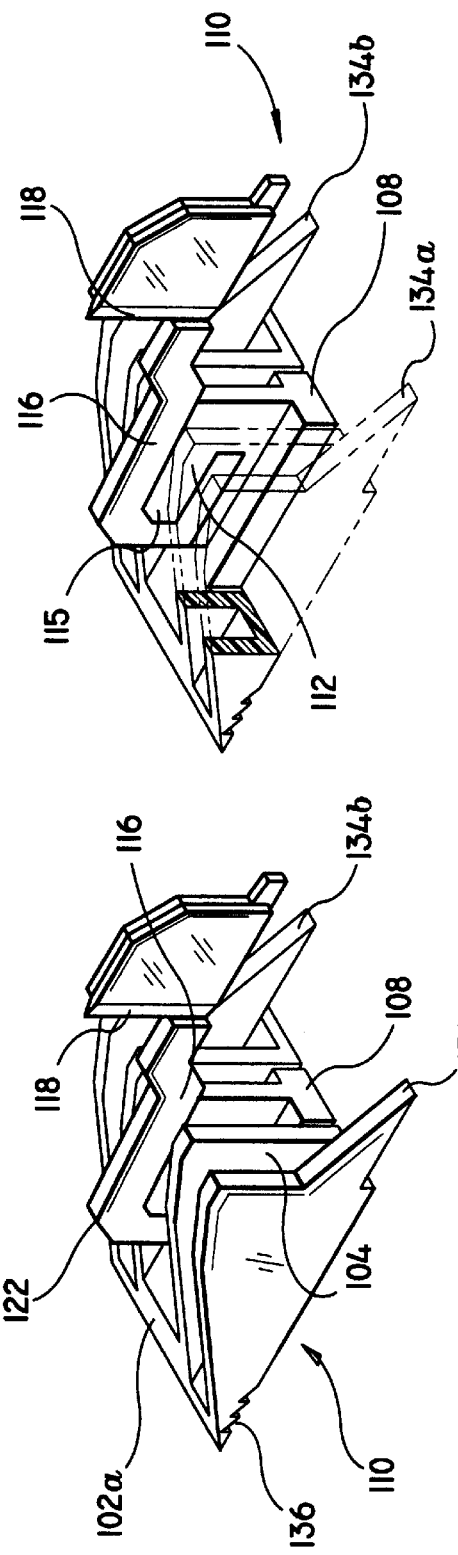

Referring to FIG. 9, the advantageous displacement of knife blade 118 is caused by the interaction of an angled cam surface 122 (FIG. 8) formed at a leading edge of blade support 116 and an angled abutment surface 124 formed at the distal end of staple cartridge body 130. During a fastening operation, when cam surface 122 initially engages abutment surface 124, the beam section 108 of actuator 110 is in substantially planar alignment with base portion 102, as illustrated in FIGS. 10A and 10B. As actuator 110 continues to translate distally within staple cartridge body 130, further interaction between cam surface 122 and abutment surface 124 causes beam section 108 to deflect angularly away from base portion 102. Preferably, beam section 108 is caused to deflect sufficiently so that the entire knife blade 118 is withdrawn into staple cartridge body 130 beneath tissue contacting surface 120, as illustrated in FIGS. 11A–11B. During the angular deflection of beam section 108, the forces generated by the interaction of cam surface 122 and abutment surface 124 can be counteracted by a pair of opposed support wings 134a and 134b which depend proximally from actuator 110 and contact the floor of housing 128. Support wings 134a and b are preferably formed monolithically with actuator 110.

Figure 14:
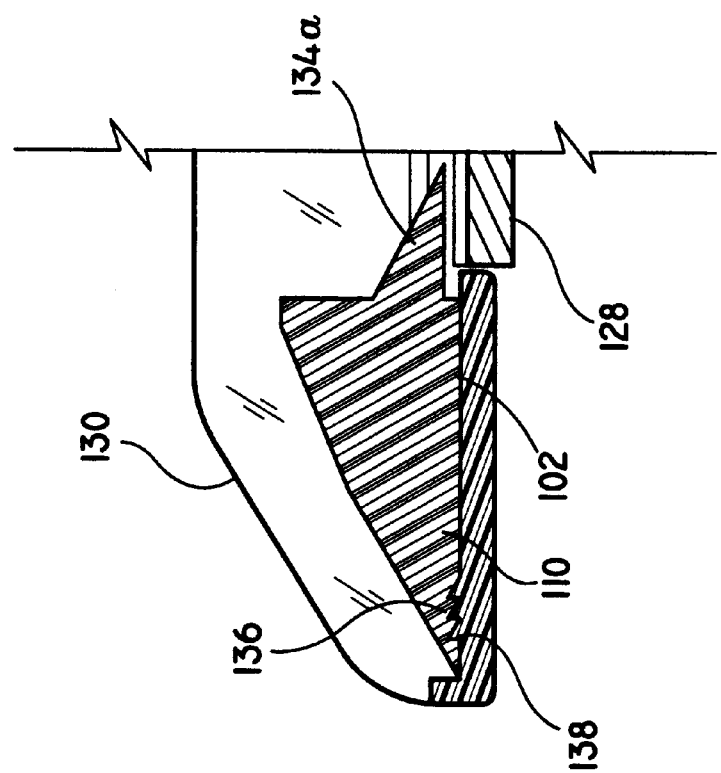
FIG. 14 is a cross-sectional view of the disposable loading unit taken along line 14—14 of FIG. 13 illustrating the actuator in a locked position at the distal end of the disposable loading unit.
Figure 13:
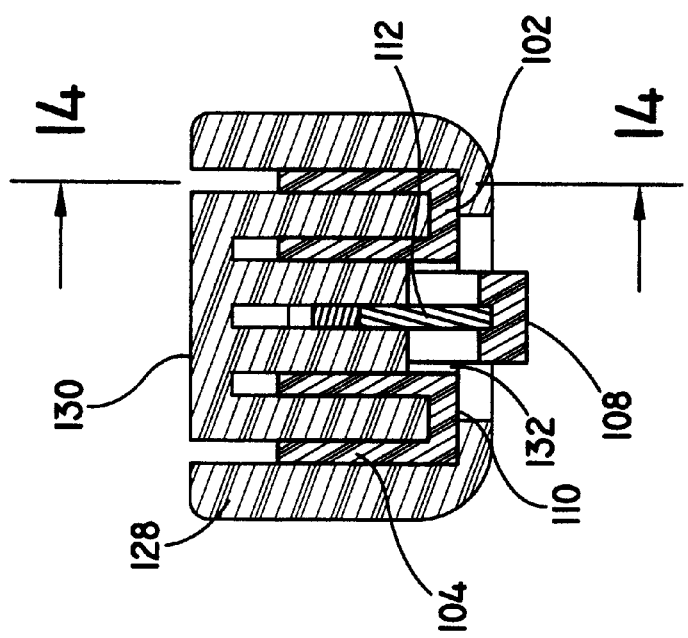
FIG. 13 is a cross-sectional view of the disposable loading unit taken along line 13—13 of FIG. 12A.

Referring to FIGS. 13 and 14, when actuator 110 reaches its distal-most position within pathway 132 of staple cartridge body 130, a plurality of angular ridges 136 formed on base portion 102 are engaged by a plurality of corresponding angular teeth 138 formed on staple cartridge body 130. At such a time, actuator 110 is fixedly retained at the distal end of the staple cartridge body 130 and cannot be withdrawn therefrom. Ridges 136 and teeth 138 prevent the actuator and associated knife blade from becoming dislodged from the staple cartridge body after it has been discarded. Of course, ridges 136 and teeth 138 can be interchanged or other structures to prevent dislodgment of the actuator can be used.

Referring now to FIGS. 15 and 16, there is illustrated the actuation mechanism for effecting the longitudinal translation of actuator 110 during a fastening operation, and for preventing the actuation of surgical apparatus 10 after actuator 110 has been driven through staple cartridge body 130. The actuation mechanism includes an elongated actuation channel 150 that translates in a longitudinal direction in response to manipulation of actuation handle 24 (See FIG. 1). Actuation channel 150 is preferably U-shaped and is configured to interact with a first camming wing 152 extending integrally from the proximal end of staple cartridge body 130, and a second camming wing 154 extending integrally from the proximal end of actuator 110.

As illustrated in FIG. 15, at the beginning of a fastening operation, as actuation channel 150 translates distally, it initially encounters the first camming wing 152 of staple cartridge body 130. Camming wing 152 guides channel 150 toward the second camming wing 154 of actuator 110, against the bias of an integral leaf spring 156 extending from actuation channel 150. Alternatively, the channel could be cambered to eliminate the need for leaf spring 156. As actuation channel 150 continues to travel distally, guided by camming wing 152, it encounters the second camming wing 154 and is guided into contact with a proximal portion of base portion 102 of actuator 110, as illustrated in FIG. 16. Thereafter, continued distal translation of actuation channel 150 drives actuator 110 through staple cartridge body 130 to sequentially eject surgical fasteners therefrom, as illustrated, for example, in FIGS. 3–5.

Figure 19:
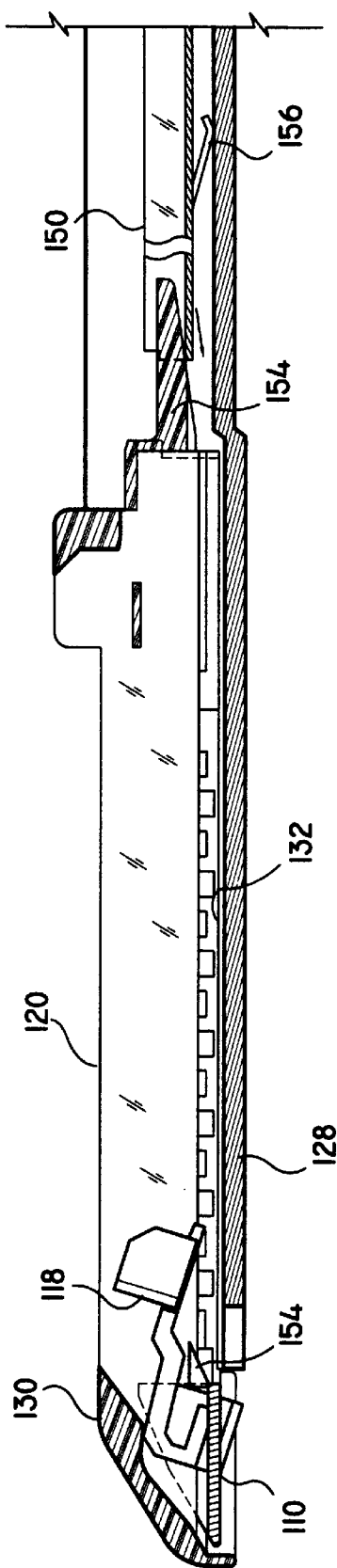
FIG. 19 is a side elevational view of the disposable loading unit illustrated in FIG. 18 wherein the actuation channel is engaged with a camming member extending from the rear end portion of the staple cartridge body.
Figure 20:
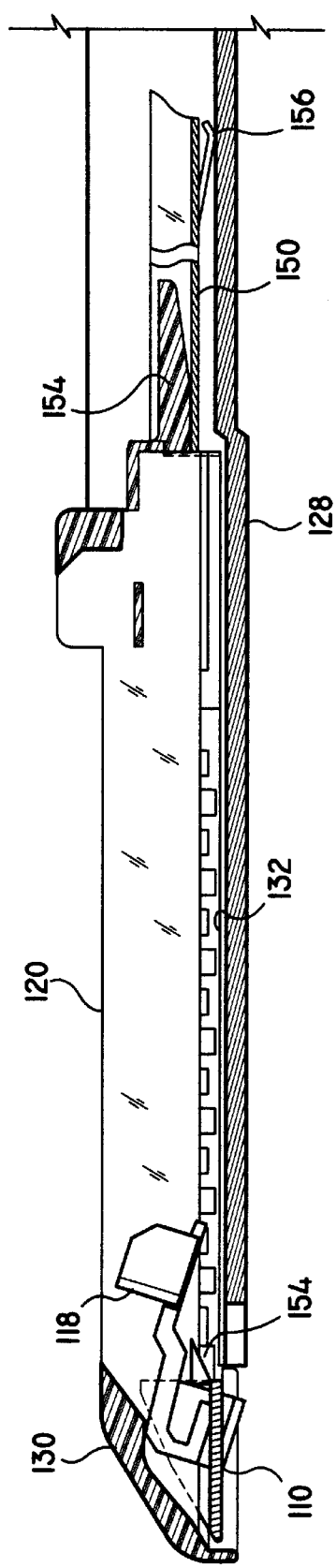
FIG. 20 is a side elevational view of the disposable loading unit illustrated in FIG. 18 wherein a distal end of the actuation channel is in abutment with a proximal end portion of the staple cartridge body.
Figure 21:
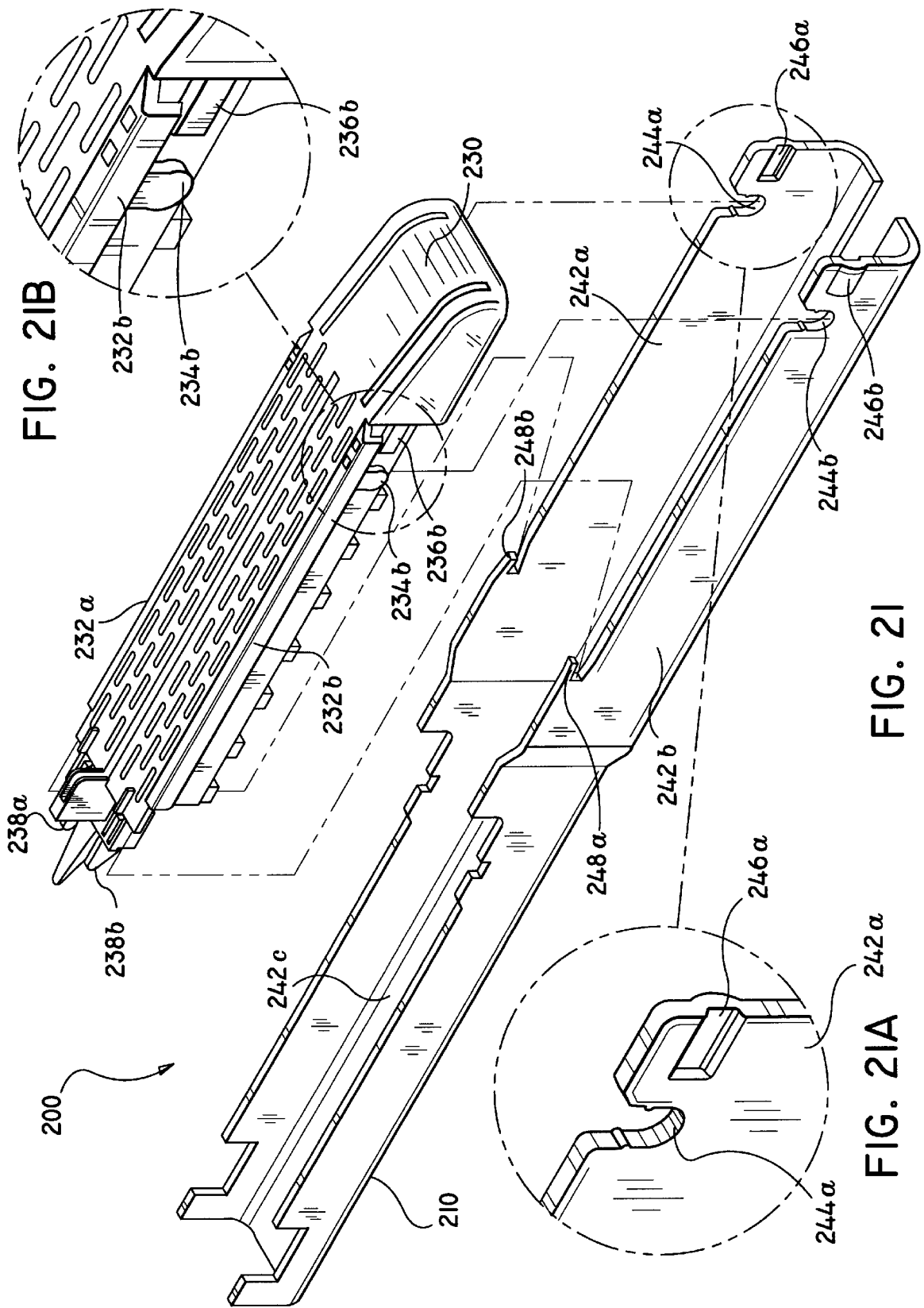
FIG. 21 is an exploded perspective view of a disposable loading unit and a housing constructed in accordance with a preferred embodiment illustrating structures for inhibiting movement of the disposable loading unit relative to the housing during a fastening operation.

Referring to FIGS. 17 and 18, at the conclusion of a fastening operation, actuator 110 is disposed within the distal end portion of staple cartridge body 130, knife blade 118 is moved out of intersection with tissue contacting surface 120, and actuation channel 150 is retracted proximally to the position illustrated in FIG. 18. In this position, actuation channel 150 is biased into engagement with the first camming wing 152 by leaf spring 156, or by its natural camber. If, at such a time, actuation channel 150 is driven distally, it will interact with the first camming wing 152, as shown in FIG. 19, but will be unable to interact with the second camming wing 154 of actuator 110. Thus, as illustrated in FIG. 20, the distal end of actuation channel 150 will abut and engage the proximal end of staple cartridge body 130 and will be prevented from translating distally. Actuation channel 150 will remain inoperative until the disposable loading unit from which fasteners have been expelled is removed from housing 128 and replaced with a new disposable loading unit having an actuator and knife disposed in a proximal position. As will be appreciated, if less than all fasteners are ejected from the staple cartridge and actuation handle 24 is released by the operator, the channel will return to the position shown in FIG. 18 and will be unable to re-enter the staple cartridge body. This desirably prevents re-use of a partially fired staple cartridge.

Referring now to FIGS. 21, 21A, 21B, and 22, an alternative disposable loading unit and housing constructed in accordance with a preferred embodiment are illustrated and are designated by reference numerals 200 and 210 respectively. Disposable loading unit 200 and housing 210 are provided with cooperative structures which function to releasably secure disposable loading unit 200 within housing 210 and inhibit lateral, longitudinal, and elevational movement of the disposable loading unit during a stapling procedure. In particular, disposable loading unit 200 includes a staple cartridge body 230 having opposed lateral struts 232a and 232b which are formed monolithically therewith and which extend substantially along the length thereof and define channels 233a (not shown) and 233b. Struts 232a and 232b releasably engage the upper portion of opposed side walls 242a and 242b of housing 210 and inhibit movement of the disposable loading unit within housing 210.

A pair of opposed detents 234a (not shown) and 234b are formed adjacent the distal end of staple cartridge body 230 for engaging a pair of corresponding notches 244a and 244b formed in the opposed side walls 242a and 242b of housing 210. The notches and the detents are configured to lockingly engage with each other and inhibit longitudinal or distal-to-proximal movement of the disposable loading unit within housing 210. In addition, a pair of outwardly depending protuberances 236a (not shown) and 236b are formed on staple cartridge body 230 for engaging a pair of corresponding depressions 246a and 246b formed in the opposed side walls 242a and 242b of housing 210. The protuberances and depressions are configured to inhibit vertical or elevational movement of the disposable loading unit within housing 210.

Figure 22:
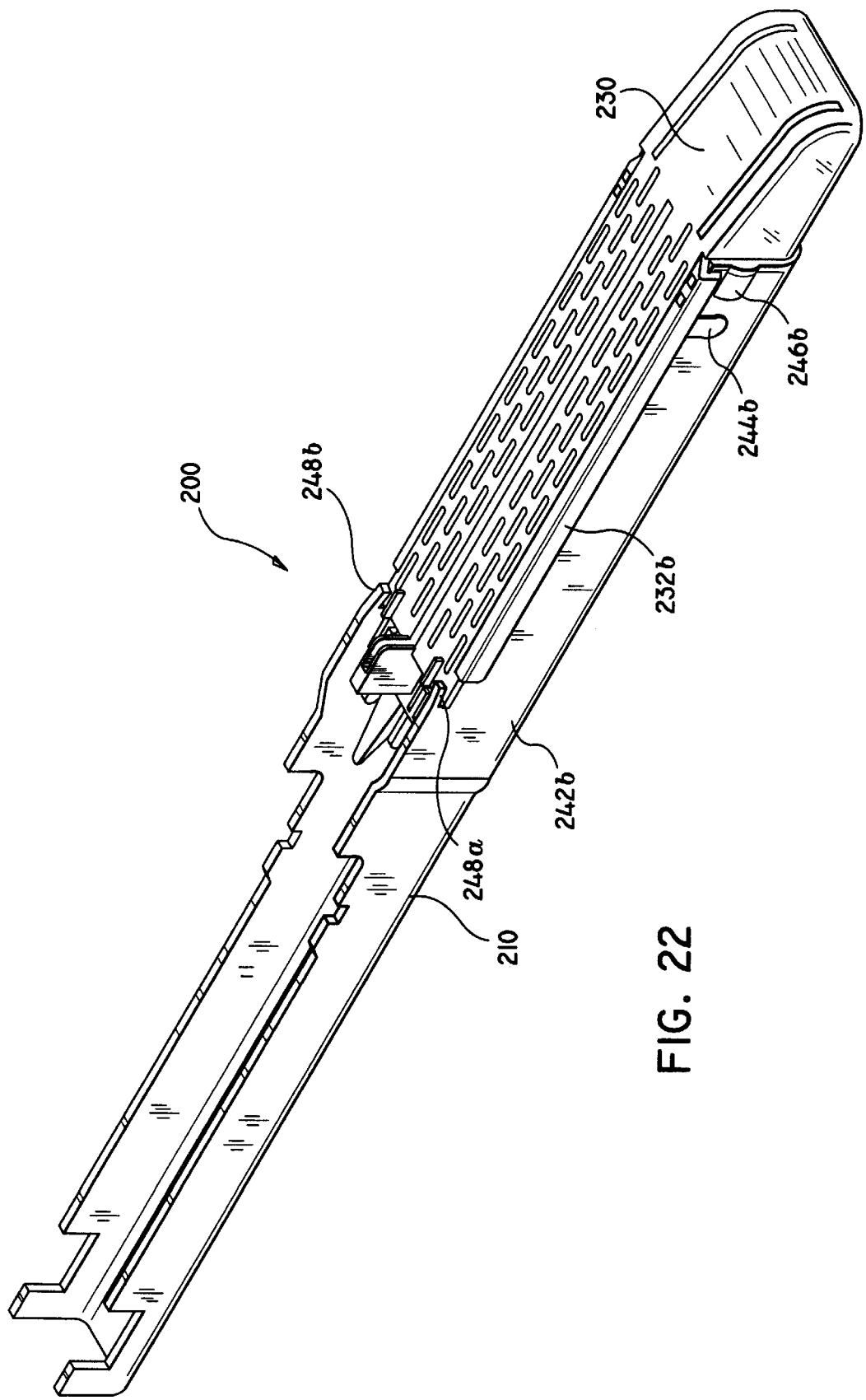
FIG. 22 is a perspective view of the disposable loading unit and the housing illustrated in FIG. 21 in an assembled condition.

Cartridge body 230 further includes a pair of proximally extending guide wings 238a and 238b which serve to guide staple cartridge body 230 into housing 210 during assembly. More particularly, guide wings 238a and 238b have respective angled guide surfaces which are dimensioned and configured to cause the proximal end of staple cartridge body 230 to slide relative to the floor 242c of housing 210 as the staple cartridge body is engaged beneath a pair of inwardly extending housing projections 248a and 248b (FIG. 22).

Referring now to FIGS. 23a–23c, there is illustrated another actuator constructed in accordance with an alternative embodiment and designated generally by reference numeral 310. Actuator 310 is configured to translate through staple cartridge body 230 in the same manner as actuator 110 to sequentially eject a plurality of surgical fasteners therefrom, and includes a base portion 312, a first set of upstanding cam plates 314a and 314b, and a second set of upstanding cam plates 316a and 316b. Cam plates 314a and 314b preferably have generally flat top portions 320 and have a leading edge 322 disposed distal of both base portion 312 and leading edge 324 of cam plates 314a and 314b. The first set of cam plates are advantageously offset or staggered from the second set of cam plates to balance the fastener driving forces generated within the disposable loading unit during a fastening operation.

As used in the claims, "securing means" is intended to refer to ridges 136 and teeth 138 formed on actuator 110 and pathway 132, respectively, and equivalents thereof.

As used in the claims, "camming means" is intended to refer to the camming wings of the actuator and equivalents thereof.

Although the foregoing description contains many specifics with respect to preferred embodiments, it will be readily apparent to those having ordinary skill in the art that changes and modifications may be made thereto without departing from the spirit or scope of the subject invention as defined by the appended claims. By way of example only, it is contemplated that the housing can be permanently mounted to the stapling apparatus with the disposable loading unit removably mounted thereto. Alternatively, the disposable loading unit can further include the housing, such that the housing is removably mounted to the stapling apparatus. It also is contemplated that greater or fewer cam plates can be included on the actuator.

We claim:

1. A disposable loading unit for a surgical stapling apparatus comprising:
   a) a staple cartridge body having a longitudinal pathway extending therethrough and a plurality of spaced apart retention slots defined therein, each supporting a respective surgical fastener;
   b) a plurality of fastener ejection members disposed adjacent the plurality of spaced apart retention slots and communicating with the longitudinal pathway;
   c) an actuator at least partially disposed within the staple cartridge body and configured to be translated through the longitudinal pathway to contact the fastener ejection members and thereby sequentially eject the surgical fasteners from their respective retention slots, the actuator including a base portion defining a plane and having at least two upstanding parallel cam plates each defining an angled leading edge for contacting the fastener ejection members;
   d) a cutting member configured to translate through the staple cartridge body, the cutting member having a blade and a blade support, the blade support including a camming surface spaced from the blade configured to interact with an abutment surface defined within a distal end portion of the staple cartridge body, wherein the staple cartridge body includes a planar tissue contacting surface through which extends a linear slot to accommodate translation of the cutting member, the planar tissue contacting surface defining a tissue contacting plane, the cutting member intersecting the tissue contacting plane during the translation thereof, and moving out of intersection with the tissue contacting plane when the camming surface of the cutting member contacts the abutment surface of the staple cartridge body.

2. A disposable loading unit according to claim 1, wherein the cutting member is pivotably supported at least partially within the staple cartridge body.

3. A disposable loading unit according to claim 2, wherein the cutting member is pivotably supported by the actuator about a pivot axis located distally of the blade.

4. A disposable loading unit for a surgical stapling apparatus comprising:
   a) a staple cartridge body having a longitudinal pathway extending therethrough and at least two rows of spaced apart retention slots defined therein, each slot supporting a respective surgical fastener, the staple cartridge body defining a planar tissue contacting surface having a linear slot extending therethrough, the staple cartridge body further defining an abutment surface formed near a distal end thereof;
   b) a plurality of fastener ejection members disposed adjacent the spaced apart retention slots and communicating with the longitudinal pathway;
   c) an actuator at least partially disposed within the staple cartridge body, the actuator having:
      i) a base portion; and
      ii) at least two upstanding parallel cam plates extending from a base portion, each of the at least two cam plates defining an angled leading edge, such that the angled leading edges are longitudinally aligned with the at least two rows of spaced apart retention slots so as to contact the fastener ejection members upon translational movement of the actuator through the longitudinal pathway and to thereby sequentially eject the surgical fasteners from their respective retention slots; and
   d) a cutting member pivotably mounted with respect to the actuator and translatably slidable with the actuator in the linear slot of the staple cartridge body, the cutting member having a blade and a flange including an upper surface which interacts with the abutment surface of the staple cartridge body, the flange being spaced distally of the blade, the cutting member being pivotable from a first position intersecting a tissue contacting plane defined by the planar tissue cutting surface, to a second position out of intersection with the tissue contacting plane, the cutting member being pivotable to the second position when the camming surface of the cutting member contacts the abutment surface of the staple cartridge body.

* * * * *